United States Patent [19]

Demarne et al.

[11] 4,435,426
[45] Mar. 6, 1984

[54] ETHERS OF PHENOL ACTIVE ON THE CARDIOVASCULAR SYSTEM, PROCESS FOR PREPARING SAME AND USE THEREOF IN DRUGS

[75] Inventors: Henri Demarne; Jean Wagnon, both of Montpellier, France

[73] Assignee: Societe Anonyme called: Sanofi, France

[21] Appl. No.: 381,796

[22] Filed: May 25, 1982

[30] Foreign Application Priority Data

Jun. 5, 1981 [FR] France .................................. 81 11242

[51] Int. Cl.³ ..................... C07C 97/10; A61K 31/165
[52] U.S. Cl. ..................................... 424/324; 424/330; 564/349; 564/222; 564/351
[58] Field of Search ...................... 564/349, 351, 222; 424/330, 324

[56] References Cited

U.S. PATENT DOCUMENTS

| | | | |
|---|---|---|---|
| 3,641,152 | 2/1972 | Shauel et al. | 564/349 |
| 3,732,308 | 5/1973 | Lauria et al. | 564/349 |
| 3,829,498 | 8/1974 | Genzer et al. | 564/345 |
| 3,935,267 | 1/1976 | Hauck et al. | 564/349 |
| 4,048,231 | 9/1977 | Hauck et al. | 564/349 |
| 4,275,058 | 6/1981 | Tucker | 564/351 |
| 4,322,370 | 3/1982 | Gardner | 424/330 |
| 4,322,432 | 3/1982 | Berthold et al. | 564/349 |

FOREIGN PATENT DOCUMENTS

| | | | |
|---|---|---|---|
| 1023214 | 3/1966 | United Kingdom | 564/349 |
| 1069343 | 5/1967 | United Kingdom | 564/349 |
| 1160448 | 8/1969 | United Kingdom | 564/349 |

OTHER PUBLICATIONS

Fieser et al., "Reagents for Org. Syn.", John Wiley & Son, pp. 1049-1050, (1967).

*Primary Examiner*—James H. Reamer
*Attorney, Agent, or Firm*—Ostrolenk, Faber, Gerb & Soffen

[57] ABSTRACT

The present invention relates to novel products, responding to general formula:

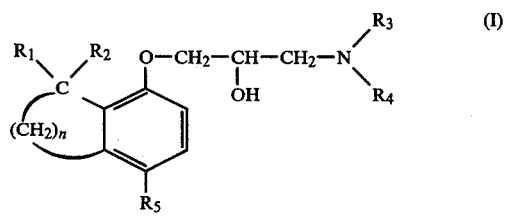

in which $R_1$ and $R_2$ taken together represent an atom of oxygen =O or $R_1$ represents hydrogen and $R_2$ represents an OH radical, $R_3$ designates an atom of hydrogen or a straight or branched alkyl radical, or an alkynyl group having from 1 to 6 atoms of carbon, $R_4$ represents a straight or branched alkyl radical having from 1 to 6 atoms of carbon, $R_5$ designates an atom of hydrogen, an alkyl group having from 1 to 4 atoms of carbon or an acylamine group and n=3 or 4; as well as to the acid addition salts of said products, to a process for preparing said products and to drugs, particularly active on the cardiovascular system, containing at least one of said products.

22 Claims, No Drawings

ETHERS OF PHENOL ACTIVE ON THE CARDIOVASCULAR SYSTEM, PROCESS FOR PREPARING SAME AND USE THEREOF IN DRUGS

The present invention relates as new industrial products to chemical substances derived from ethers of phenols as well as to their acid addition salts and the optical isomers of said derivatives.

The invention also relates to a process for preparing novel compounds and to the application thereof in therapeutics.

The compounds according to the invention are selected from the group constituted by:

(a) the racemics and optical isomers responding to the general formula:

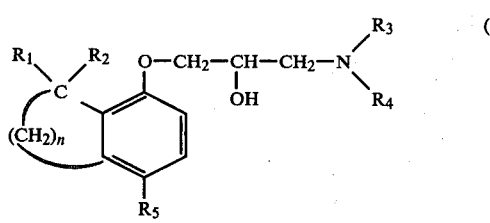

in which:

$R_1$ and $R_2$ taken together represent an atom of oxygen =O or $R_1$ represents hydrogen and $R_2$ represents an OH radical, $R_3$ designates an atom of hydrogen or a straight or branched alkyl radical having from 1 to 6 atoms of carbon, $R_4$ represents a straight or branched alkyl radical having from 1 to 6 atoms of carbon, or an alkynyl group having 2 to 6 atoms of carbon, $R_5$ designates an atom of hydrogen, an alkyl group having from 1 to 4 atoms of carbon or an acylamino group, n=3 or 4;

(b) their acid addition salts.

Compounds (I) where $R_1$ and $R_2$ represent an atom of oxygen are obtained in two steps from ortho hydroxylated ketones 1, according to the reaction scheme:

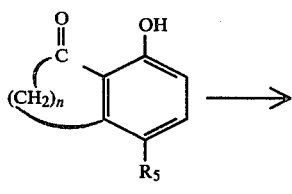

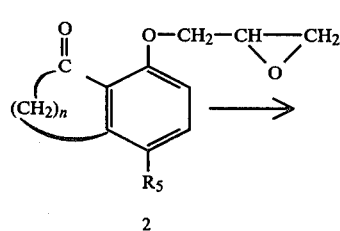

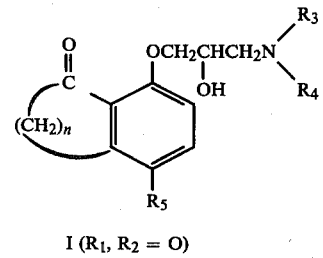

When n=3, the ketones 1 are known and described in chemical literature, for example in The Journal of Organic Chemistry 28, 325 (1963) and in the Journal of Chemical Society 1964, 2816.

When n=4, the ketone 1 may be obtained from orthobromoanisole and cyclopentanone subsequent to following reactions:

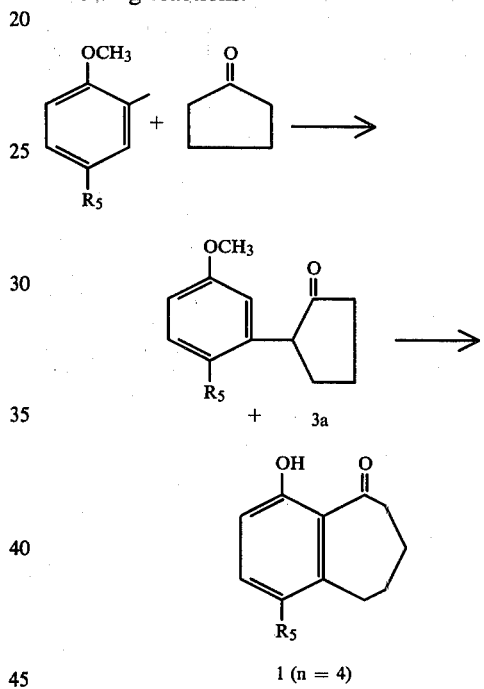

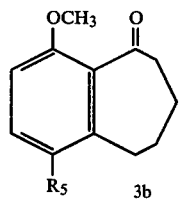

The obtaining of the mixture of ketones 3 had been described in Tetrahedron 21, 95 (1972), but it is difficult to separate the constituents.

It has been found that, by action of a demethylation agent, such as boron tribromide on the mixture of the two ketones, only compound 3b is demethylated whilst 3a is decomposed. It is then easy to separate the two constituents of the mixture and to obtain the product 1 (n=4) with a yield of about 50%.

From the ketones 1, the action of the epichlorohydrin in the presence of an alkaline agent such as sodium hydroxide within a solvent such as water, ethanol or a polyalcohol such as diethyleneglycol or an ether of polyol such as 2-methoxy ethanol, at a temperature of between 50° and 120° C., leads to the epoxides 2. The opening of these epoxides 2 by an amine

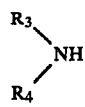

within a solvent such as a lower aliphatic alcohol such as ethanol, at a temperature of between 50° and 120° C., leads to compounds (I). By subsequent reduction, for example by sodium borohydride in a lower aliphatic alcohol, the compounds (I) are obtained in which $R_1=H$ and $R_2=OH$.

In all cases, by action on the compounds (I) of a mineral or organic acid within an appropriate solvent, the corresponding salts are obtained.

The separation of the optical isomers present in products (I) may if necessary be effected according to a known method, by treating the racemic product with an optically active acid such as one of the D and L tartric, D and L di-benzoyltartric or D and L di-p-toluoyltartric acids.

The following examples illustrate the invention.

EXAMPLE 1

1-(8-oxo 5,6,7,8-tetrahydro 1-naphthyl oxy) 2-hydroxy 3-tertiobutylamino propane (a) 1-(8-oxo 5,6,7,8-tetrahydro 1-naphthyl oxy) 2,3-epoxy propane To the solution heated to 80° C. of 3.2 g of 8-hydroxy 1-tetralone and 20 ml of epichlorohydrin in 20 ml of 2-methoxy ethanol is added 1.8 g of sodium hydroxide and the mixture is heated to reflux for 1 hour. Water is added and the mixture is extracted with methylene chloride. The organic phase is separated, dried and the solvent is evaporated.

The residue is chromatographed over a silica column and, by elution with methylene chloride, 3 g of the expected product are obtained, which are used as such for the following step.

(b) CM 7285

The mixture of 3 g of the epoxide obtained hereinabove and 2.5 g of tertiobutylamine in 50 ml of absolute ethanol is heated to reflux for 3 hours. The solvent is evaporated and the residue is taken up in dilute hydrochloric acid. The aqueous phase is extracted with ether then is alkalized up to pH 9. It is extracted with ether, the solution is dried and the solvent is evaporated.

The solid residue is recrystallized in isopropylic ether and yields cream crystals (1.6 g); m.p.: 76°-80° C.

EXAMPLE 2

4-(3-tertiobutylamino 2-hydroxy propoxy) 6,7,8,9-tetrahydro 5-5H-benzocycloheptenone (Code No. CM 7630; I $R_1R_2=O$, $R_3=H$, $R_4=C(CH_3)_3$, n=4 $R_5=H$)

(a) 4-hydroxy 6,7,8,9-tetrahydro 5-5H-benzocycloheptenone (1 n=4)

A mixture of ketones 3a and 3b is prepared according to P. Caubert et col., Tetrahedron 21, 95, 1972, from orthobromoanisole and cyclopentanone; b.p./1.2 mmHG: 124°-130° C.

To a solution of 4.2 g of the preceding mixture in 50 ml of methylene chloride cooled to 0° C. is added, in 10 mins., the solution of 11 g of boron tribromide in methylene chloride and then the mixture is left to stand for 40 hrs. at ambient temperature. The solution is poured into water and neutralised by addition of sodium bicarbonate. The aqueous phase is extracted with methylene chloride and filtered over a silica column. By elution by an 8:2 vol/vol petroleum ether-ether mixture, the expected phenol is obtained (2.15 g) in the form of an oil characterised by its IR spectrum and its NMR spectrum.

(b) 4-(2,3-epoxy propoxy) 6,7,8,9-tetrahydro 5-5H-benzocycloheptenone (2 n=4)

The mixture of 2 g of phenol obtained hereinabove, 25 ml of epichlorohydrin and 1.2 g of sodium hydroxide in 25 ml of 2-methoxy ethanol is heated to reflux for 4 hrs. Water is added and then it is extracted with ether.

The solution is washed with water, dried over sodium sulfate and the solvent is evaporated to dryness.

The residue is used as such for the following step.

(c) CM 7630

The residue of the preceding step (2.5 g) is dissolved in 35 ml of absolute ethanol. 1.5 g of tertiobutylamine is added and taken to reflux for 4 hours. The solvent is evaporated to dryness and the residue is taken up in dilute hydrochloric acid. The aqueous phase is extracted with ether then is alkalized by sodium carbonate. A solid is separated which is recrystallized in isopropylic ether.

Colourless crystals are obtained (1.7 g); m.p.: 74.5°-76° C.

EXAMPLE 3

1-(8-hydroxy 5,6,7,8-tetrahydro 1-naphthyl oxy) 2-hydroxy 3-tertiobutylamino propane, acid fumarate Code No.: CM 7633; I $R_1=H$, $R_2=OH$, $R_3=H$, $R_4=C(CH_3)_3$ (n=3), $R_5=H$ 1.5 g of the compound of Example 1 is dissolved in 20 ml of methanol and the mixture is cooled to 0° C. and then the solution of 1.5 g of sodium borohydride is added in 20 ml of water and stirring is effected for 2 hours at 0° C.

The excess of borohydride is destroyed by adding a small quantity of ethyl acetate, and then the mixture is diluted with water and the methanol is evaporated. The aqueous phase is extracted with ether and then the ethereal solution is extracted with a dilute solution of hydrochloric acid. The hydrochloric solution is alkalized by sodium carbonate. The mixture is extracted with ether, dried over sodium sulfate and the solvent is evaporated to dryness.

An oil remains which is converted into acid fumarate by adding a stoichiometric quantity of fumaric acid dissolved in the minimum of ethanol.

The crystals are dried and recrystallized in the absolute ethanol-isopropylic ether mixture.

Finally, crystals are obtained (1.7 g); m.p.: 161°-164° C.

EXAMPLES 4 TO 13

By operating as in Examples 1 and 2, but by varying the amine

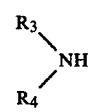

and/or the starting product 1, the products are obtained whose characteristics are gathered together in Table 1 hereinbelow.

EXAMPLES 14 TO 17

By operating as in Example 3, but by varying the starting ketonic compound, the products mentioned in Table II hereinbelow are obtained.

The products of the invention were subjected to the pharmacodynamic tests mentioned hereinafter.

PHARMACOLOGICAL ACTION IN THE DOG

The dog is anaesthetized with sodium pentobarbital administered intravenously at the dose of 30 mg/kg. A canula placed in the short saphenous vein allows the products to be injected intravenously. The animal is

TABLE I $$-N \begin{matrix} R_3 \\ \diagdown \\ R_4 \end{matrix}$$

| Example n° | Code No. | $R_1, R_2$ | $R_5$ | n | $R_4$ | Salt or base (recrystallization solvent) | m.p. (°C.) |
|---|---|---|---|---|---|---|---|
| 4 | 7331 | =O | H | 3 | $-NH-CH(CH_3)_2$ | Base (methylene chloride-isopropylic ether) | 65 |
| 5 | 7632 | =O | H | 3 | $-N(H)-C(CH_3)(C_2H_5)-$ (i.e. $-NH-C(CH_3)(C_2H_5)$ with CH$_3$) | Acid fumarate (ethanol-ethyl acetate) | 136–138 |
| 6 | 7692 | =O | H | 4 | $-NH-C(CH_3)(C_2H_5)$ with CH$_3$ | Base (hexane-isopropylic ether) | 52–53 |
| 7 | 7700 | =O | $-NH-COCH_3$ | 3 | $-NH-CH(CH_3)_2$ | Base (methanol-isopropylic ether) | 175–177 |
| 8 | 7706 | =O | $-CH_3$ | 3 | $-NH-C(CH_3)_3$ | Acid fumarate (ethanol-ethyl acetate) | 234–235 |
| 9 | 7709 | =O | H | 4 | $-NH-CH(CH_3)_2$ | Acid fumarate (acetone) | 174–178 |
| 10 | 7713 | =O | $-CH_3$ | 3 | $-NHCH_2-CH(CH_3)_2$ | Base (hexane) | 93–94 |
| 11 | 7760 | =O | $-CH_3$ | 3 | $-NH-C(CH_3)_2-C\equiv CH$ | Acid fumarate (ethyl acetate ethanol) | 142 |
| 12 | 7994 | =O | H | 4 | $-NH-C(CH_3)_2-C\equiv CH$ | Acid fumarate (methanol, acetone, ethyl acetate) | 135–137 |
| 13 | 7995 | =O | H | 4 | $NH-CH_2CH(CH_3)_2$ | Acid fumarate (methanol, ethyl acetate) | 157–159 |

TABLE II $$-N \begin{matrix} R_3 \\ \diagdown \\ R_4 \end{matrix}$$

| Example n° | Code No. | $R_1, R_2$ | $R_5$ | n | $R_4$ | Salt or base (recrystallization solvent) | m.p. (°C.) |
|---|---|---|---|---|---|---|---|
| 14 | 7693 | H, OH | H | 4 | $-NH-C(CH_3)_3$ | Base (1st isomer) (isopropylic ether, hexane) | 142–144 |
| 15 | 7694 | " | " | " | " | Base (2nd isomer) (hexane-isopropylic ether) | 108–110 |
| 16 | 7707 | H, OH | $-CH_3$ | 3 | $-NH-C(CH_3)_3$ | Acid fumarate (ethyl acetate, ethanol) | 161–162 |
| 17 | 7800 | H, OH | $-CH_3$ | 3 | $-NH-C(CH_3)_2-C\equiv CH$ | Acid fumarate (ethanol) | 153 |

The products of the invention were studied with a view to determining their pharmacological activity and, more particularly, their activity on the cardiovascular system.

intubed and breathes spontaneously.

The cardiac frequency and the systemic arterial pressure are studied and the variations of these parameters are observed after intravenous injection of the product to be tested, each product being injected at increasing doses.

ANTAGONISM OF THE EFFECTS OF ISOPRENALINE

The antagonism of the products vis-a-vis the β stimulant cardiovascular effects of isoprenaline on the adrenergic β receptors was sought. The results are shown in Table below and expressed in ID 50: this is the dose expressed in mg/kg which provokes 50% inhibition of tachycardia ($\beta_1$) and of hypertension ($\beta_2$) induced by the isoprenaline administered by intravenous route.

ANTAGONISM OF THE EFFECTS OF NORADRENALINE

The antagonism of the products vis-a-vis the vascular effects provoked by intravenous administration of noradrenaline on the adrenergic α receptors was sought. The results set forth in the Table below are expressed in ID 50, i.e. the dose (mg/kg) which provokes the 50% inhibition of pressor response due to the intravenous administration of noradrenaline.

| Code No. Products | ID 50 isoprenaline $\beta_1$ | ID 50 isoprenaline $\beta_2$ | ID 50 noradrenaline mg/kg (pressor response) |
|---|---|---|---|
| 7285 | 0.03 to 0.1 | 0.03 | 0.3 to 3 |
| 7630 | 0.01 to 0.03 | 0.01 to 0.03 | 0.03 to 0.1 |
| 7632 | 0.01 to 0.1 | 0.01 to 0.1 | 0.03 to >0.1 |
| 7694 | 0.03 to 0.1 | 0.01 to 0.03 | 0.1 to 0.3 |
| 7706 | 0.1 | 0.01 | 0.03 to 0.3 |
| 7760 | 0.1 | 0.03 | 0.1 to 0.3 |

It emerges from these results that the products according to the invention are particularly active as antagonists of the β stimulant effects of the isoprenaline on the adrenergic β receptors and as antagonists of the β stimulant effects of the noradrenaline on the adrenergic β receptors.

Certain products provoke a bradycardia and/or provoke a reduction in the systemic arterial pressure in the anaesthetized animal.

Furthermore, these products are non-toxic. They may therefore be used for the following therapeutic indications:

treatment of pathological disorders in connection with a hyperproduction of catecholamines: tachycardias, palpitations, extrasystoles, hypertension;

basic treatment of anginous disease, sequelae of infarct, disorders in the auricular and ventricular rhythm;

basic treatment of hypertensive disorders;

treatment of different neurological disorders: isolated states of anxiety or with organic localisation, cures of detoxication, etc.

They may be presented in the different forms of oral administration, such as tablets dosed at 1 to 10 mg, rectal administration such as suppositories dosed at 1 to 10 mg and injectable preparations containing from 0.5 to 5 mg of active ingredient.

The usual dosage is from 1 to 2 tablets at 5 mg per day, but, exceptionally, under medical control, it may exceed this figure.

A few examples of Galenic preparation are given hereinafter:

| Tablets | |
|---|---|
| CM 7630 | 5 mg |
| Microcrystalline cellulose | 160 mg |
| Lactose | 187 mg |
| Magnesium stearate | 8 mg |
| | 360 mg |

| Suppositories | | |
|---|---|---|
| CM 7630 | | 10 mg |
| Suppocire C (injectable mixture of natural fatty acid esters) Labrafil 2130 C (interesterified hydrogenated palm oil) | qsp | 3 mg |

What is claimed is:

1. Novel products, responding to general formula:

$$\text{(I)}$$

in which:

R$_1$ and R$_2$ taken together represent an atom of oxygen =O or R$_1$ represents hydrogen and R$_2$ represents an OH radical, R$_3$ designates an atom of hydrogen or a straight or branched alkyl radical having from 1 to 6 atoms of carbon, R$_4$ represents a straight or branched alkyl radical having from 1 to 6 atoms of carbon, or an alkynyl group having 2 to 6 atoms of carbon, R$_5$ designates an atom of hydrogen, an alkyl group having from 1 to 4 atoms of carbon or an acylamine group, n=3 or 4;

as well as the mineral acid or organic acid addition salts of said products.

2. The novel products of claim 1, wherein they are in the form of one of their optical isomers.

3. Drug particularly active on the cardiovascular system, wherein it contains, an adrenergic blocking effective amount of as active substance, the product of one of claims 1 and 2.

4. The drug of claim 3, wherein it is prepared for administration in oral form at a rate of 1 to 10 mg of active ingredient per day, in the form of suppositories at a rate of 0.5 to 5 mg of active ingredient per day, or in injectable form at a rate of 1 to 10 mg of active ingredient per day.

5. Novel products according to claim 1 wherein R$_1$ and R$_2$ together represent an atom of oxygen =O; R$_3$ is hydrogen; R$_4$ is selected from the group consisting of —CH(CH$_3$)$_2$; —C(CH$_3$)$_3$; —C(CH$_2$)$_2$C$_2$H$_5$, —CH$_2$CH(CH$_3$)$_2$, and —C(CH$_3$)$_2$C≡CH; and R$_5$ is hydrogen, methyl or —NHCOCH$_3$.

6. The novel products of claim 1 wherein R$_1$ represents hydrogen, R$_2$ represents an OH radical, R$_3$ is hydrogen, R$_4$ is —C(CH$_3$)$_3$ or —C(CH$_3$)$_2$C≡CH and R$_5$ is hydrogen or methyl.

7. 1-(8-oxo 5,6,7,8-tetrahydro 1-naphthyl oxy) 2-hydroxy 3-tertiobutylamino propane according to claim 1.

8. 4-(3-tert iobutylamino 2-hydroxy propoxy) 6,7,8,9-tetrahydro 5-5H-benzocycloheptenone according to claim 1.

9. 1-(8-hydroxy 5,6,7,8-tetrahydro 1-naphtyl oxy) 2-hydroxy 3-tertiobutylamino propane, acid fumarate according to claim 1.

10. The novel products of claim 1 wherein n is 3, $R_1$ and $R_2$ taken together represent an atom of oxygen =O, $R_3$ is hydrogen, $R_4$ is —C(CH$_3$)$_2$C$_2$H$_5$, —C(CH$_3$)$_3$ or —C(CH$_3$)$_2$—C≡CH, and $R_5$ is hydrogen or methyl.

11. The novel products of claim 1 wherein $R_1$ is hydrogen, $R_2$ is hydroxyl, $R_3$ is hydrogen, $R_4$ is —C(CH$_3$)$_3$, $R_5$ is hydrogen and n is 4.

12. The novel products of claim 1 wherein n is 4.

13. The drug of claim 3 wherein said product is 4-(3-tertiobutylamino 2-hydroxy propoxy) 6,7,8,9-tetrahydro 5-5H-benzocycloheptenone.

14. The drug of claim 3 wherein said product is 1-(8-oxo 5,6,7,8-tetrahydro 1-naphthyl oxy) 2-hydroxy 3-tert iobutylamino propane.

15. The drug of claim 3 wherein $R_1$ is hydrogen, $R_2$ is hydroxyl, $R_3$ is hydrogen, $R_4$ is —C(CH$_3$)$_3$, $R_5$ is hydrogen and n is 4.

16. Process for preparing the products of claim 1 comprising the steps of reacting a ketone of the formula

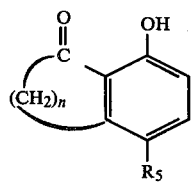

with epichlorohydrin in the presence of an alkaline agent within a solvent at 50°-120° C. and thereafter reacting the product obtained with an amine of the formula

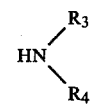

at 50°-120° C.

17. The process of claim 16 wherein the product of the reaction with the amine is reduced by treatment with sodium borohydride.

18. The process of claim 17 wherein the optically active resulting products are separated by resolving the racematic reaction product with the aid of an optically active acid.

19. In the method of treating a cardiovascular ailment with an adrenergic blocking effective amount of an active substance, the improvement which comprises employing the product of one of claims 1 or 2 as said active substance.

20. The method of claim 19 wherein said product is that where n is 3, $R_1$ and $R_2$ taken together represent an atom of oxygen =O, $R_3$ is hydrogen, $R_4$ is —CH(CH$_3$)$_2$C$_2$H$_5$, —C(CH$_3$)$_3$ or —C(CH$_3$)$_2$—C≡CH, and $R_5$ is hydrogen or methyl; or where $R_1$ is hydrogen, $R_2$ is hydroxyl, $R_3$ is hydrogen, $R_4$ is —C(CH$_3$)$_3$, $R_5$ is hydrogen and n is 4.

21. The method of claim 19 wherein said product is 1-(8-oxo 5,6,7,8-tetrahydro 1-naphthyl oxy) 2-hydroxy 3-tertiobutylamino propane, 4-(3-tertiobutylamino 2-hydroxy propoxy) 6,7,8,9-tetrahydro 5-5H-benzocycloheptenone or 1-(8-hydroxy 5,6,7,8-tetrahydro 1-naphthyl oxy) 2-hydroxy 3-tertiobutylamino propane.

22. The method of claim 19 wherein said product is in oral form containing 1-10 mg of active ingredient; in the form of suppositories, containing 0.5-5 mg of active ingredient; or in injectable form containing 1-10 mg of active ingredient.

* * * * *